United States Patent [19]

Au

[11] 4,178,940
[45] Dec. 18, 1979

[54] PRESSURE CONTROL SYSTEMS

[76] Inventor: Anthony S. Au, P.O. Box 2593, Station A, Sudbury, Ontario, Canada, P3A 4S9

[21] Appl. No.: 877,986

[22] Filed: Feb. 15, 1978

Related U.S. Application Data

[63] Continuation-in-part of Ser. No. 809,802, Jun. 24, 1977.

[51] Int. Cl.² ............................................ A61M 25/00
[52] U.S. Cl. ................................. 128/207.15; 251/61.1
[58] Field of Search ............ 128/351, 349 B, 349 BV, 128/344, 208, 342, 2.05 S; 251/61.1

[56] References Cited

U.S. PATENT DOCUMENTS

| | | | |
|---|---|---|---|
| 2,990,252 | 6/1961 | Gelden et al. | 251/61.1 X |
| 3,064,935 | 11/1962 | Collins | 251/61.1 |
| 3,502,297 | 3/1970 | Wardrup | 251/61.1 X |
| 3,504,676 | 4/1970 | Lomholt | 128/351 |
| 3,693,611 | 9/1972 | Ploss | 251/61.1 X |
| 3,794,043 | 2/1974 | McGinnis | 128/351 X |
| 4,005,701 | 2/1977 | Aisenberg et al. | 128/2.05 S |
| 4,044,793 | 8/1977 | Krueger | 128/351 X |

FOREIGN PATENT DOCUMENTS 2055049 12/1971 Fed. Rep. of Germany ........... 128/351

Primary Examiner—Henry J. Recla
Attorney, Agent, or Firm—Fetherstonhaugh & Co.

[57] ABSTRACT

A pneumatically controlled pressure relief valve and various systems incorporating a pneumatically controlled pressure relief valve. The valve has a flexible valve closure member which is expandable to close a through passage of the valve and includes a pressure chamber disposed externally of the valve passage and isolated from the through passage by the flexible valve closure member so that the valve may open and close in response to the differential between the pressure in the pressure chamber and the pressure in the through passage of the valve. An input passage opens into the pressure chamber for admitting air and a manually operable valve is provided for opening and closing the input passage to regulate the admission of air. The systems incorporating the valve include an inflatable cuff system for a tracheal or endotracheal tube, a positive end expiratory pressure system and a suction system incorporating a suction catheter.

4 Claims, 14 Drawing Figures

U.S. Patent  Dec. 18, 1979  Sheet 1 of 4  4,178,940
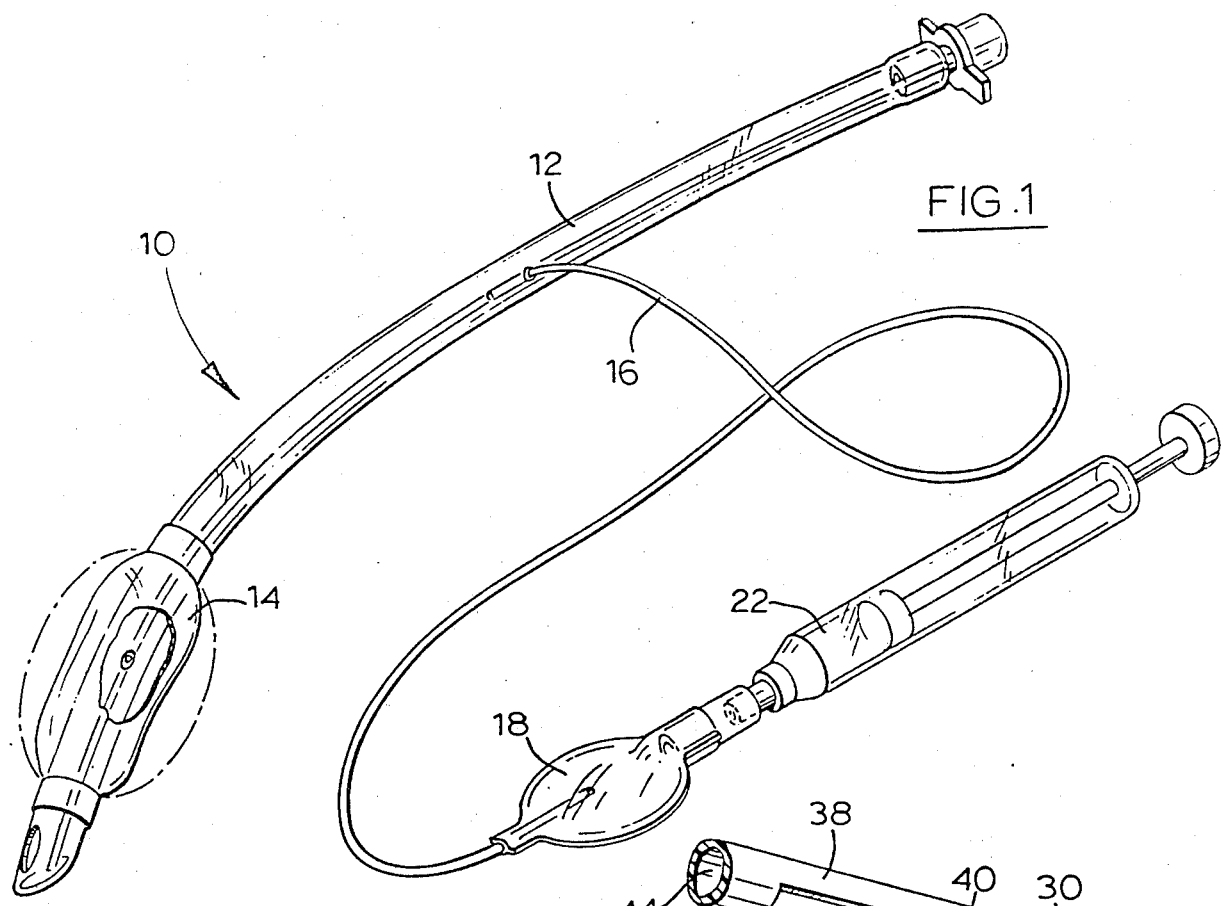
FIG.1
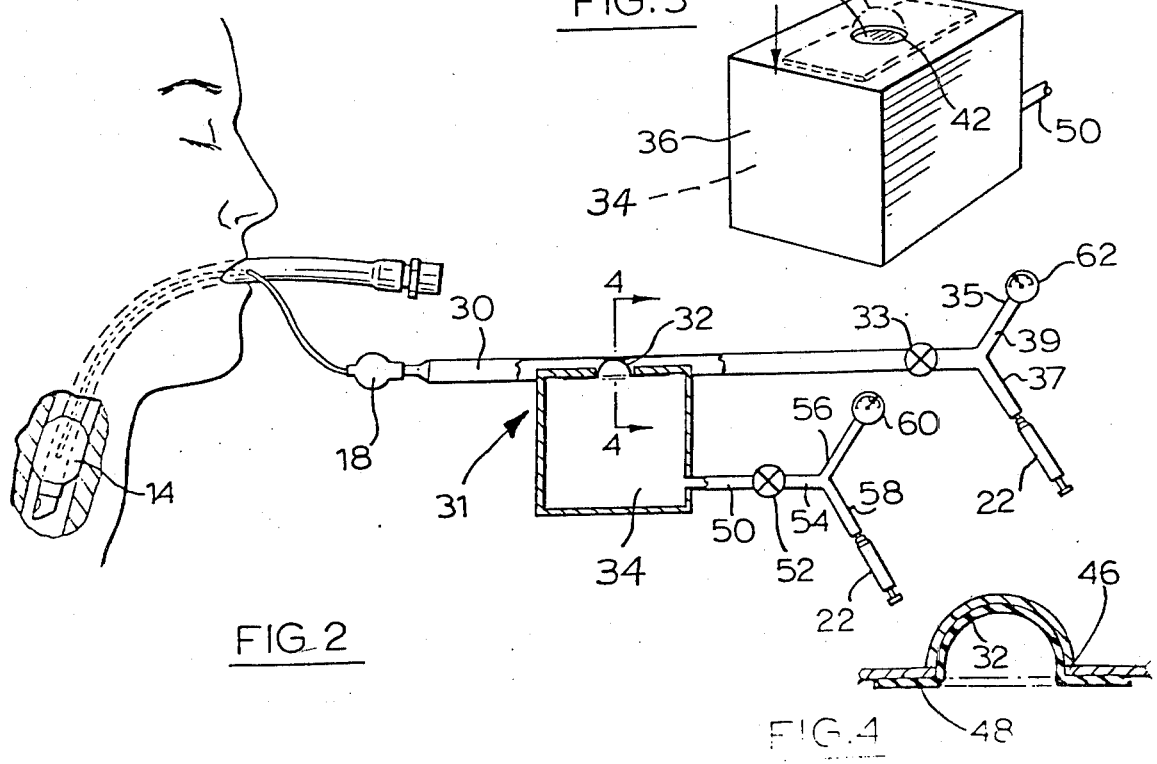
FIG.2
FIG.3
FIG.4

PRESSURE CONTROL SYSTEMS

FIELD OF INVENTION

This invention relates to pneumatically controlled pressure relief valves and systems employing such valves and is a continuation-in-part of application Ser. No. 809,802, filed June 24, 1977. In particular, this invention relates to a pneumatically controlled pressure relief valve and an inflatable cuff system of a tracheal, endotracheal or endobronchial tube or the like, a positive end expiratory system, suction system, each of the systems being improved by the use of a pneumatically controlled pressure relief valve.

PRIOR ART

Pneumatic valves which employ a diaphragm for opening and closing a through passage in response to pressure variations in various systems have been known for many years. In most instances, the diaphragm forms the actuating mechanism for actuating a mechanical valve closure member.

A number of special purpose diaphragm control valves have been developed in which the diaphragm member itself is expandable to directly control the flow of fluid through a valve. One such device is illustrated in U.S. Pat. No. 2,598,207, E. G. Bailey et al, dated May 27, 1952. In this device, a bladder is located within a conduit and the bladder is inflatable to restrict the flow of fluid through the conduit. The extent to which the bladder is inflated is determined by pressure within the conduit in use and is controlled by a pressure regulator. The pressure regulator includes a complex system of moving parts which add to its cost and is not compatible with pressure systems such as those employed in medical applications such as the inflation of a cuff of a tracheal or endotracheal tube. The valving system of the Bailey et al patent is particularly adapted for use in industry in that the pressure regulator is of a type commonly used in industry.

In the medical field, tracheal intubation, also known as endotracheal intubation, has always carried with it the risk of tracheal damage. The risk of tracheal damage increases with increased duration of intubation and, more importantly, with an increase in the pressure in the cuff of the tracheal tube. Despite various modifications in the cuffs of tracheal tubes and despite meticulous care in avoiding over-inflation of the cuffs of the tracheal tubes, complications still occur. Previous modifications to tracheal tubes have included the provision of high volume, low pressure cuff systems. However, such systems have not eliminated the tracheal damage problem. One cause of tracheal damage is believed to be the initial high pressure in the cuff of the tracheal tube during the initial inflation of the cuff. Damage can also result in circumstances where the pressure of the cuff is initially quite low but increases during surgery because of diffusion of anaesthetic gases (e.g. nitrous oxide, oxygen and other anaesthetic gases) into the cuff. In circumstances where patients are intubated as, for example, when patients are receiving intensive care, despite meticulous monitoring of their cuff pressures in an intensive care unit prior to surgical operations the cuff pressures may increase during and after their operations as a result of diffusion of gases into the cuffs as described above.

Despite the existence of problems related to tracheal damage resulting from cuff pressure for some considerable time, no simple and effective pressure release system has been proposed for use in such systems. The pneumatic valve of the present invention is particularly suitable for use in an inflatable cuff system of a tracheal intubation or endotracheal intubation system in that it is compatible with such a system and in that the control pressure applied to the pneumatic valve may be applied by a syringe of the type used to inflate the cuff. The valve also lends itself to use with appropriate manometers for measuring the cuff inflation pressure and regulating pressure applied to the valve. The valve may also be readily adapted to provide for a simultaneous inflation of the cuff and pressurizing of the pressure chamber of the valve used to regulate the relief pressure of the valve.

Because an increase in pressure can result in tracheal damage, it is important that any pressure relief valve used in such a system must be extremely sensitive. The pneumatic valve of the present invention employs a pressure chamber of substantial volume so that the diaphragm which closes the valve can be moved to an open position without causing any great increase in pressure in the pressure chamber. For this reason, the capacity of the pressure chamber is preferably several times greater than the increase caused by the expansion of the diaphragm to its position closing the valve.

The pneumatic valve of the present invention is also suitable for use in maintaining a positive end expiratory pressure in treating patients with cardio-pulmonary deseases. The value of a positive end expiratory pressure (P.E.E.P.) in the treatment of patients with cardio-pulmonary deseases has been clearly established. This P.E.E.P. is usually achieved by using valves employing weights or diaphragms and springs or by immersing the expiratory limb of the patient's breathing circuit in water. The problem with the use of weighted valve mechanisms is that their operation may be adversely influenced by a change in position of the valves and, as a result, difficulty is experienced during the transportation of patients. The problem with the use of valves employing diaphragms and springs in combination is that such valves are subject to breakage of the springs and inaccuracy of pressure regulation due to changes in spring elasticity. In addition, such mechanisms are not compatible with medical systems as a whole.

In suction systems in which suction is applied to a suction catheter or the like, it is frequently important to ensure that excessive suction is not applied by the catheter. Again, a pressure release pneumatic valve constructed in accordance with a further embodiment of the present invention can be used to advantage in such a system. The pressure release valve which will normally close a vent passage in such a system and which will open to vent the suction system when the pressure in the system drops below a predetermined level thereby limiting the negative pressure which may by applied by the suction machine to the system.

SUMMARY OF INVENTION

According to one aspect of the present invention, there is provided a pneumatic valve which comprises a through passage having an input end and an output end, a valve passage opening into said through passage, a flexible valve closure member mounted at said valve passage, said flexible valve closure member being expandable from a first position permitting free flow of fluid through said through passage to a second position closing said through passage, a pressure chamber disposed externally of said valve passage and isolated from said through passage by said flexible valve closure member whereby said flexible valve closure member may be moved between said first and second positions in response to variations in the differential between the pressure in said pressure chamber and the pressure in said through passage, input passage means opening into said pressure chamber for admitting air to and venting air from said pressure chamber, valve means for opening and closing said input passage to regulate the admission of air to and venting of air from said pressure chamber.

According to a further aspect of the present invention, there is provided in an inflatable cuff system of a tracheal or endotracheal tube having an inflation passage communicating with the inflatable cuff, the improvement of a pneumatic valve comprising a pressure chamber, a valve closure member adapted to open and close said inflation passage in response to a pressure differential between said inflation passage and said pressure chamber, input passage means opening into said pressure chamber for admitting air to said pressure chamber to pressurize said chamber to set the pressure at which the valve closure member will open to vent said inflatable cuff system, and means for selectively opening and closing said input passage means.

According to yet another aspect of the present invention there is provided in an expiratory system having an expiratory passage, the improvement of means for generating a positive end expiratory pressure comprising a pneumatic valve comprising a pressure chamber, a valve closure member adapted to open and close said expiratory passage in response to a pressure differential between said expiratory passage and said pressure chamber, input passage means opening into said pressure chamber for admitting air to said pressure chamber to pressurize said chamber to set the pressure at which the valve closure member will open to vent said expiratory system and means for selectively opening and closing said input passage means.

According to yet another aspect of the present invention, there is provided in a suction system including suction passage means connecting a suctioning device such as a suction catheter or the like to a suction source, the improvement of, a vent passage having one end communicating with said suction passage and another end through which venting is provided, a pneumatic valve in said vent passage, said pneumatic valve having a pressure chamber and an inflatable valve closure member adapted to be inflated to extend into said vent passage by pressure applied thereto by said pressure chamber, said inflatable valve closure member being movable between a first position in which said vent passage is open and a second position in which said vent passage is closed in response to a predetermined pressure variation in said vent passage.

According to a further aspect of the present invention, there is provided in a pressure system, the improvement of a vent passage opening from the pressure system, a pneumatic valve in said vent passage, said pneumatic valve having a pressure chamber and an inflatable valve closure member adapted to be inflated to extend into said vent passage by pressure applied thereto by said pressure chamber, said inflatable valve closure member being movable between a first position in which said vent passage is open and a second position in which said vent passage is closed in response to a predetermined pressure variation in said vent passage.

PREFERRED EMBODIMENTS

The invention will be more clearly understood after reference to the following detailed specification read in conjunction with the drawings, wherein;

FIG. 1 is a pictorial view of a cuffed endotracheal tube system and an inflating syringe of a type in association with which the valve of the present invention may be employed;

FIG. 2 is a diagrammatic illustration of a tracheal tube system incorporating a pneumatic valve according to an embodiment of the present invention;

FIG. 3 is an exploded view of a pneumatic pressure release valve according to an embodiment of the present invention;

FIG. 4 is a sectional view along the line 4—4 of FIG. 2;

Figure 5:
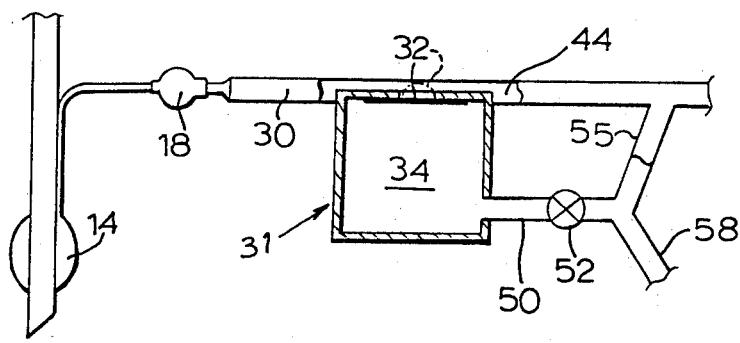
FIGS. 5 through 10 illustrate various systems for charging the pneumatic pressure release valve and its associated system which is to be vented.

With reference to FIG. 1 of the drawings, the reference numeral 10 refers generally to an assembly which includes a cuffed endotracheal tube and a syringe for inflating the cuff.

The system includes an endotracheal tube 12 which has an inflatable cuff 14 and a cuff inflation tube 16 which extends from the cuff 14 through a portion of the body of the tube 12 to a pilot cuff bladder 18. The pilot cuff bladder 18 is adapted to receive one end of an inflating syringe 22. The cuff 14 can be inflated by operating the inflating syringe 22. When the cuff 14 is inflated, the pilot cuff bladder 18 is also inflated. The pilot cuff bladder 18 provides visible indication that the cuff 14 is inflated.

A pneumatically controlled pressure relief valve constructed in accordance with an embodiment of the present invention and used in association with an endotracheal tube as illustrated in FIG. 2 of the drawings and generally identified by the reference numeral 31.

As shown in FIG. 3 the pressure relief valve 31 comprises a tubular portion 30, a flexible valve closure member 32 and a pressure chamber 34. The tubular member 30 has a portion 38 of semi-circular cross-section which opens outwardly at 40 from the through passage 44.

The pressure chamber 34 is located within a housing 36 which is formed with a circular valve passage 42 at the upper end thereof. The radius of the circular valve passage 42 corresponds to the radius of the portion 38. The housing 36 is proportioned to fit within the recess 47 formed in the tubular member 30. The flexible valve closure member 32 is preferably made from readily extensible flexible diaphragm material which is impermeable to the ambient gas or fluid used in the system to ensure that diffusion of gas or fluid through the diaphragm does not occur. The valve closure member 32 has a peripheral edge portion 48 (FIG. 4) extending around the periphery of the valve passage 42. The valve closure member 32 is extensible from the relaxed position shown in chain lines in FIG. 4 and shown in solid lines in FIG. 3 to the extended position shown in FIG. 4 in which it extends into the through passage 44 of the tubular member to close the through passage 44. The peripheral edge portion 48 of the valve closure member 32 may be adhesively secured or otherwise suitably clamped by a mounting plate to the adjacent side wall of the housing 36 so that the peripheral edge portion is restrained when the central portion of the valve closure member 32 is expanded into the through passage 44.

Air is admitted to the pressure chamber 34 through an input passage 50. In the embodiment shown in FIG. 2, a check valve 52 is provided for opening and closing the input passage 50. A Y-shaped piece 54 is connected to the valve 52 and has passages 56 and 58 opening therethrough. A manometer 60 is connected to the end of the passage 56 and the passage 58 is adapted to receive an inflating syringe 22.

Closure valve 33 is located in the tubular member 30 and serves to selectively open and close the passage 44 downstream of the flexible valve closure member 32. A Y-piece 39 is located at the end of the tubular member 30 and has passages 35 and 37 opening therethrough.

In a pressure release valve constructed substantially in accordance with FIGS. 2, 3 and 4 of the drawings, it is anticipated that the pressure in the tubular member 30 required to deflect the valve closure member 32 to an open position will be substantially equal to the pressure in the pressure chamber 34. In other embodiments, however, the pressure required to open the valve may be different to that required in the tubular portion 30. In all constructions the valve may be calibrated prior to its use to establish the pressure required in the pressure chamber 34 to permit release of the pressure in the tubular member 30.

In the use of a pressure release valve constructed in accordance with FIGS. 2, 3 and 4 of the drawings in a pressure system such as that illustrated in FIG. 2 in which the pressure release valve has been calibrated to indicate that the valve closure member 32 will open to relieve pressure when the pressure in the tubular member 30 exceeds that of the pressure chamber 34, a manometer is connected to the passage 35 of the Y-piece 39 and an inflating syringe 22 is connected to the passage 37. With the valve 33 in the open position, the cuff of the tracheal tube is inflated by injecting air from the syringe 22 to achieve said required seal. The attending physician is able to determine when the required seal is obtained by auscultation. The pressure reading on the manometer 62 is noted when the required seal is obtained and the syringe 22 is removed from the arm 37. The valve 33 remains in the open position with the result that the cuff is permitted to deflate. By reference to previous calibrations it is possible to determine the pressure required in the pressure chamber 34 to cause the diaphragm 32 to expand to close the through passage of the tubular member 30 to obtain the required sealing pressure in the cuff 14. A manometer 60 is connected to the passage 56 of the Y-piece 54 and an inflating syringe 22 is connected to the passage 58. The valve 52 is moved to the open position and the pressure chamber 34 is pressurized by the inflating syringe 22 until the required pressure is obtained as determined by the reading on the manometer 60. The valve 52 is then closed and the inflating syringe 22 removed. Thereafter the tracheal tube 34 is reinflated by means of an inflating syringe 22 connected to the passage 37 as previously described. Thus, if the pressure in the cuff 14 exceeds a predetermined level, the valve closure member 32 will be deflected inwardly to permit venting of the cuff to prevent an excessive build-up of pressure in the cuff 14.

In some instances, the attending physician may wish to maintain a pressure in the cuff in excess of the minimum pressure required to obtain a seal at the cuff. In such circumstances, the pressure release valve of the present invention may be pressurized to the calibrated pressure corresponding to the required pressure in the system.

As previously indicated, the capacity of the pressure chamber 34 is substantially greater than the expanded volume of the valve closure member 32 so that the pressure within the pressure chamber 34 will only increase very slightly when the valve closure member 32 is deflected inwardly to permit venting of the cuff and thus only a very slight pressure differential is required between the pressure chamber 34 and the through passage 44 to cause the valve closure member 32 to move to and fro between an open and closed position. Preferably the unexpanded volume of the pressure chamber is at least three times the increase in volume required to close the pressure release valve.

FIG. 5 of the drawings illustrates a modification in which like numerals are applied to like parts to those illustrated in FIG. 2 of the drawings. In this embodiment, a passage 55 extends between the passage 58 and the through passage 44 on the downstream side of the pressure release valve. In use, the valve 52 is located in the open position and the outer end of the through passage 44 is occluded manually or by other means. A pressure source such as an inflating syringe is connected to the passage 58 and air is injected under pressure into the cuff 14 by way of passage 55 and through passage 44 and into the pressure chamber 34 by way of passage 50. Air is injected until the pressure in the cuff of the tracheal tube is adequate to achieve a seal between the cuff and the tracheal wall. This is determined clinically as previously described. Both the cuff 14 and chamber 34 are pressurized simultaneously. When the required pressure has been obtained and the system is stabilized, the valve 52 is closed. The pressure source is disconnected from the passage 58 so that the passage 44 may be vented to atmosphere through the passage 55 and passage 58. As a result, a pressure differential is established between the passage 44 and the pressure chamber 34 sufficient to cause the flexible valve closure member 32 to extend to close the through passage 44. The occlusion at the passage 44 may then be removed or may continue so long as the passages 55 and 58 remain open to atmosphere. If and when the pressure in the cuff 14 exceeds the pressure in the pressure chamber 34, the pressure differential will cause the valve closure member 32 to move to position to permit venting of the cuff 14. To deflate the cuff 14 of the tracheal tube, the valve 52 is opened to vent the pressure chamber 34 and thus cause the valve closure member 32 to return to its relaxed configuration. This structure has the advantage that the end of the tube 44 may be permanently sealed if the passage 55 and 58 remain open to atmosphere. The permanent sealing of the through passage has the advantage of providing compactness and ease of pressurization of the cuff 14 and pressure chamber 34 without the need for a manometer. The possibility of the valve closure member 32 occluding the through passage 44 during the simultaneous pressurization of the cuff and chamber can be prevented by ensuring that the passage 50 has a smaller diameter than the passage 55.

Figure 6:
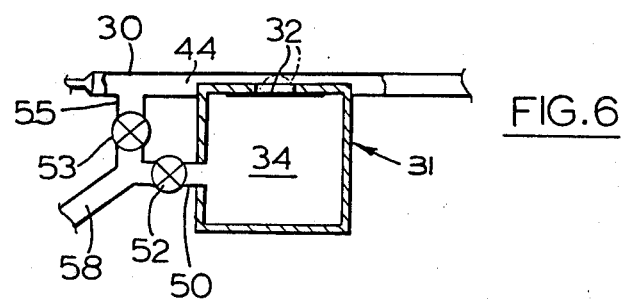

FIG. 6 of the drawings illustrates a further modification in which like numerals are applied to like parts to those illustrated in FIG. 5 of the drawings. In this embodiment, the passage 55 is connected to the through passage 44 on the upstream side of the pressure release valve and valve 53 is located in the passage 55. In use, the valves 52 and 53 are located in an open position. The free end of the through passage 44 downstream from the pressure release valve is occluded manually or by other means. A pressure source is connected to the passage 58 and air is introduced until the pressure in the system which is to be pressurized, is adequate. The valves 52 and 53 are then closed and the free end of the through passage 44 is opened. The drop in pressure resulting from the opening of the free end of the through passage 44 may cause a sufficient pressure differential between the through passage 44 and the pressure chamber 34, with the result that the diaphragm 32 will extend to close the through passage 44. If the pressure in the cuff exceeds the pressure in the pressure chamber 34, the diaphragm 32 will be deflected to permit air to escape to atmosphere. This structure has the advantage of being compact and can be operated without the aid of a manometer when pressurizing the cuff system and the pressure chamber. It will, however, be apparent that a manometer may be used in association with the system of the present invention.

Figure 7:
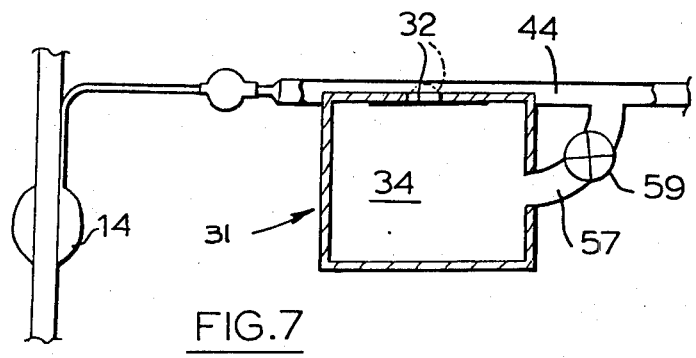

FIG. 7 of the drawings illustrates a still further modification in which like numerals are applied to like parts to those illustrated in FIG. 5 of the drawings. In this embodiment, a single passage 57 extends from the through passage 44 to the pressure chamber 34 and a closure valve 59 is located in the passage 57.

In use, the valve 59 is located in an open position to connect the through passage 44 with the pressure chamber 34. A pressure source is then applied to the open end of the through passage 44 and air is admitted at sufficient pressure to inflate the cuff 14 to achieve the required seal between the tracheal tube cuff and the tracheal wall as previously described. The pressure chamber 34 is simultaneously pressurized to the same pressure as the pressure applied to the cuff. The valve 59 is then moved to the closed position closing the passage 57 and the pressure source is then removed from the free end of the passage 44. The reduction in pressure in the through passage 44 caused by the removal of the pressure source causes the valve closure member 32 to extend to close the through passage 44. The pressure release valve 31 then operates in the manner previously described. To deflate the cuff, the valve 59 is moved to the open position opening the communication between the pressure chamber 34 and the passage 44, thereby allowing the pressure chamber 34 to be depressurized. The valve closure member 32 then returns to its relaxed configuration and the passage 44 is automatically opened.

Figure 8:
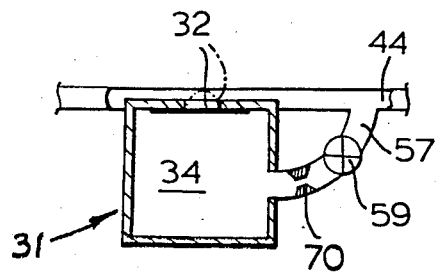

It will be understood that in each of the previous examples in which air is simultaneously supplied to pressurize the cuff 14 and to presurize the pressure chamber 34, it may be necessary to include a restriction in the passage leading to the pressure chamber to ensure that the cuff is inflated to the required pressure before the pressure release valve 31 moves to its closed position. FIG. 8 of the drawings illustrates a restriction 70 in the passage 57 of a pressure release valve constructed in accordance with FIG. 7. The restriction 70 can be proportioned to ensure that the cuff 14 or any other inflatable system is properly inflated before the pressure chamber 34 is fully pressurized and may be located at any point along the length of the passage 57.

An alternative method of ensuring correct inflation may be to proportion the pressure chamber so that it has a volume which is so much greater than the expanded volume of the cuff and the tubes leading to the cuff to ensure that the cuff system is automatically inflated before the pressure chamber is inflated. If under such circumstance, the volume of air or gas from the pressure source entering the cuff system is equal to the volume of air or gas entering the pressure chamber, the pressure inside the pressure chamber will initially be less than the pressure in the cuff system during pressurization and thus the diaphragm 32 will not move to a position closing the through passage 44. After pressurization of the cuff 14 has been completed and the pressure in the cuff system and in the pressure chamber will equalize rapidly, the valve closure member 32 can be caused to move to the closed position as a result of a minor drop in pressure in the cuff system when the pressure source is removed.

If the passage connecting the pressure chamber 34 and the pressurizing source is of a smaller diameter than the passage 44 and the passage connecting the passage 44 to the cuff, the cuff can be inflated to the required pressure before the pressure chamber 34 is fully pressurized to cause the valve closure member 32 to move to the closed position. Thus, it will be seen that various systems may be developed for preventing closure of the valve closure member 32 before the cuff has been pressurized.

In some applications, it is necessary to occlude a system at an initial pressure level and to provide a mechanism whereby the pressure in the system may be permitted to rise above the initial occluding pressure without being released until a higher predetermined pressure level is reached. For example, in a clinical situation, one might experience difficulty with the apparatus described in FIGS. 2 through 8 of the drawings in circumstances where the pressure in the cuff of an endotracheal or tracheal tube increases momentarily when a patient coughs. In these circumstances, the cuff pressure may exceed the regulating pressure and in the embodiments previously described, a portion of the pressurized medium would be vented as a result of the pressure releasing action of the pressure release valve 31. This pressure release results in a loss of volume of pressurized medium in the cuff system which is not replaced.

As a result of the permanent loss of volume the pressure in the cuff system may be decreased to an extent sufficient to deflate the cuff with the result that it is rendered ineffective. As a result, two possible complications may ensue namely aspiration which may lead to lung complications and if the patient is ventilated with a ventilator (breathing machine) a loss in ventilation may occur. These problems may be particularly acute when the apparatus is used in the care of a critically ill patient in an intensive care unit. The system illustrated in FIG. 9 of the drawings and described hereinafter serves to overcome this difficulty by providing two pressure release valves arranged in series with a reservoir located therebetween.

Figure 9:
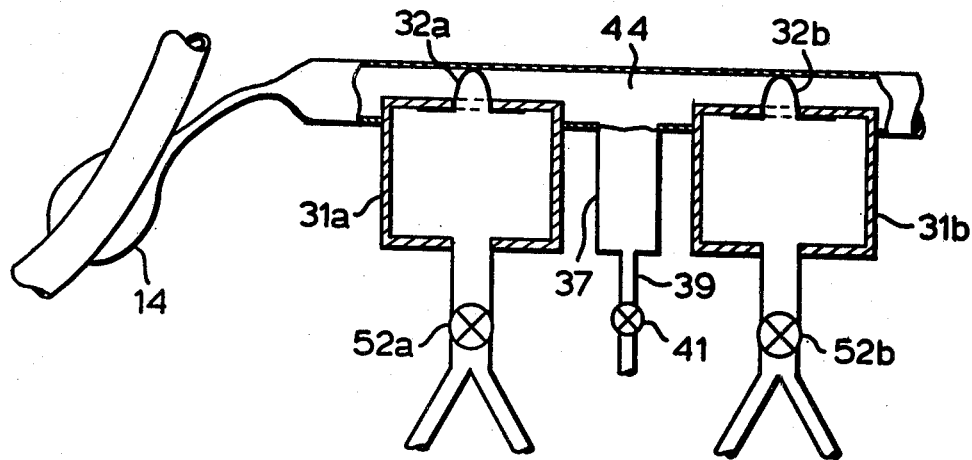

As shown in FIG. 9 of the drawings, the cuff 14 is connected to a through passage 44 and pressure release valves 31a and 31b are mounted in the through passage 44 and have valve closure members 32a and 32b respectively adapted to open or close the through passage 44 as required. Reservoir 37 is provided between the pressure release valves 31a and 31b and opens into the through passage 44. The passage 39 opens out of the reservoir and has a closure valve 41 located therein. In the embodiment illustrated in FIG. 9 of the drawings in which the medium to be pressurized is a compressible gaseous medium, the walls of the reservoir 37 may be made from an expandable elastic material or from a rigid material. In applications in which the medium is a non-compressible medium such as a non-compressible liquid such as water, the walls of the reservoir are elastic so that the reservoir is expandable. The pressure release valve 31a may be pressurized as previously described by adjustment of the check valve 52a and the pressure release valve 31b may be pressurized by control of the check valve 52b.

In use, the pressure required in the pressure release valve 31a in order to expand diaphragm 32a to close the through passage 44 and establish a pressure in the cuff system required to obtain occlusion is predetermined and the pressure required in the pressure release valve 31b to regulate the release of pressure from the reservoir system at a predetermined level above that of the cuff pressure is determined.

With both pressure release valves 31a and 31b in the open position pressure is applied to the cuff system by way of the through passage 44 by the application of a pressure source downstream from pressure release valves 31a and 31b. Thereafter the pressure release valve 31a is pressurized to the required pressure as previously determined and thereafter the pressure release valve 31b is pressurized to the required higher pressure as previously determined. Thus, the pressure in the system between cuff 14 and the first pressure release valve 31a is the same as the pressure in the system between the pressure release valves 31a and 31b.

In use, if the patient coughs, the increase in pressure in the cuff will cause the pressure release valve 31a to open to permit release of the pressure in the cuff when the pressure exceeds the predetermined set pressure established by the pressure release valve 31a. The opening of the diaphragm 32a will permit the transfer of the pressurized medium to the reservoir 37. If the volume displaced is not sufficient to increase the pressure in the reservoir above that controlled by the second pressure release valves 31b, the pressure release valve 31b will remain closed, if, however, the pressure exceeds the regulating pressure of the pressure release valves 31b, it will open to permit the medium to escape from the system. If, following the transfer of the pressurized medium from the cuff system to the reservoir, the pressure in the cuff should subsequently be reduced to a pressure below the pressure in the reservoir 37, the pressure release valve 31a may again open to permit the transfer of medium from the reservoir 37 to the cuff to increase the cuff pressure to the required regulating pressure.

Thus, it will be seen that by setting the pressure release valves 31a to a first predetermined pressure and setting the pressure release valves 31b to a second higher release pressure, it is possible to provide for the temporary reduction in pressure in the cuff system and to ensure that the pressure in the cuff system may be re-established.

Various modifications of the embodiment of the invention illustrated in FIG. 9 of the drawings are also possible. For example, the pressure release valve 31b may be omitted and the passage 44 may be permanently closed at the point where the pressure release valve 31b is located in the embodiment illustrated in FIG. 9. In such a modification, the inflating medium would be admitted to the reservoir and the cuff through valve 41. In use, this structure would provide a reservoir downstream from the pressure release valve 31a into which inflating medium may be deverted to reduce the pressure in the cuff 14 as aforesaid. This structure would be simpler to construct than that illustrated in FIG. 9 of the drawings and is particularly suitable for use in patients who require long term ventilation care but who are not anaesthetized.

Various other modifications of the device illustrated in FIG. 9 of the drawings are possible which will also provide a reservoir which is separated from the inflatable cuff by a pressure release valve so that the pressurizing medium in the cuff may be permanently or temporarily exhausted from the cuff into a holding reservoir.

From the foregoing, it will be apparent that a substantial number of systems can be developed in which a pneumatic pressure release valve can be used in association with the pressure system of an inflatable cuff of a tracheal or endotracheal tube system. The pneumatically controlled pressure release valve of the present invention has the advantage of being inflatable by inflation means compatible with equipment such as inflating syringes normally used for inflating cuffs and the like. The pneumatic pressure release valve also has the advantage that it can be used with or without a manometer in order to set the release pressure and it is unaffected by its orientation. It also has the advantage that the pressure chamber is of a substantial volume so that the deflection of the valve closure member from its closed position to its open position does not substantially increase the pressure in the pressure chamber. As a result, the valve of the present invention may be constructed so that it is extremely sensitive because the pressure variation in the pressure chamber between the open and closed positions of the valve is very small. In contrast in systems in which a bladder is located within the through passage of the valve and it is necessary to fully deflate the bladder to open the valve a considerable pressure variation is likely to result within the pressure system.

While in the embodiments of the invention described above reference is made to the inflation of a cuff of a tracheal or endotracheal tube, it will be noted that the cuff merely constitutes one pressure source which is to be regulated.

Figure 10:
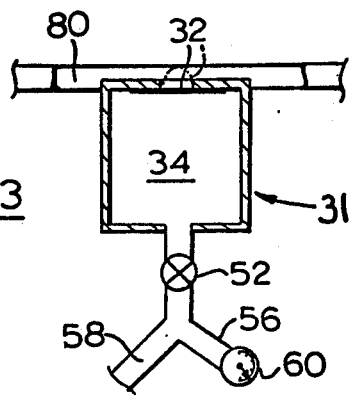

As shown in FIG. 10 of the drawings, the pressure source may be in the form of the expiratory limb 80 of a patient's breathing circuit. Under these circumstances, the chamber 34 is pressurized to a predetermined pressure with a manometer 60 measuring the predetermined pressure by way of the passage 56. Thus, the pressure release valve of the present invention will provide a positive end expiratory pressure in a patient's breathing circuit.

Figure 11:
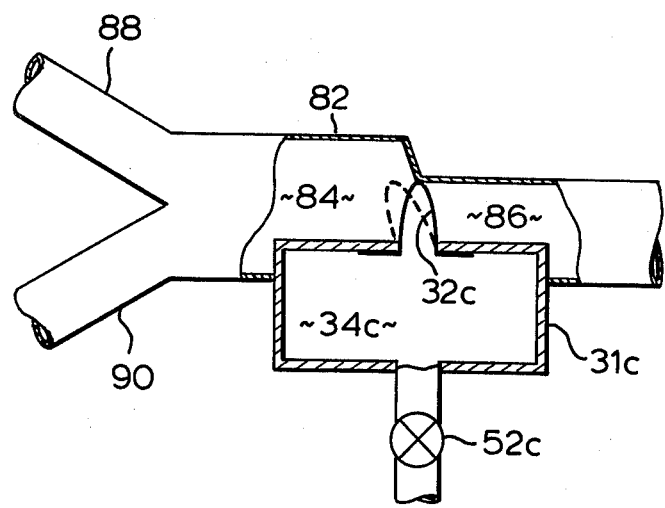
FIG. 11 illustrates a modification in which a pneumatic pressure release valve is used to control the suction applied to a suction catheter.

A pressure release valve constructed in accordance with the general principles described above may be used to provide an improved negative pressure system as described below with reference to FIG. 11 of the drawings. In FIG. 11 of the drawings, the line 82 in which pressure release valve 31c is located has an enlarged through passage 84 on one side of the flexible membrane 32c and a smaller passage 86 on the other side thereof. The passage 84 is connected by a branch passage 88 to a suction machine and by branch passage 90 to a suction catheter or the like for suctioning secretions, as for example, in the suctioning of the tracheal tube or the continuous suctioning of the gastro intestinal tract or a body cavity such as the pleural cavity. When expanded the diaphragm 32c is movable between the position shown in solid lines in FIG. 11 and the position shown in broken lines to permit and prevent communication between passages 84 and 86 depending upon the pressure differential established between passages 84 and 86. The expanded configuration of the diaphragm 32 is arranged to seat in the end of passage 86 to close the passage 86. Preferably, the diaphragm 32c and the seat formed in the end of the passage 86 are of an arcuate configuration. In use, the pressure required in the chamber 34c in order to permit the diaphragm 32c to move to the open position at the required control pressure differential is determined by precalibration and the chamber 34 is pressurized by admitting air through the inlet passage with the check valve 52c in the open position. Thereafter the check valve 52c is closed and the diaphragm 32c will remain in the position preventing communication between passages 84 and 86 until the negative pressure in passage 84 falls below a predetermined minimum at which time the diaphragm 32c may move to the open position. The pressure release valve 31c differs from that previously described in that it is not necessary to compress the atmosphere within the pressure chamber 34 in order to effect movement of the diaphragm 32 between its open and closed positions. The ability to regulate the pressure at which the diaphragm will move to and from the open position by regulating the pressure in the chamber 34c is nevertheless important in a system such as that including a suction catheter or the like in that it is compatible with these systems as a whole.

Figure 12:
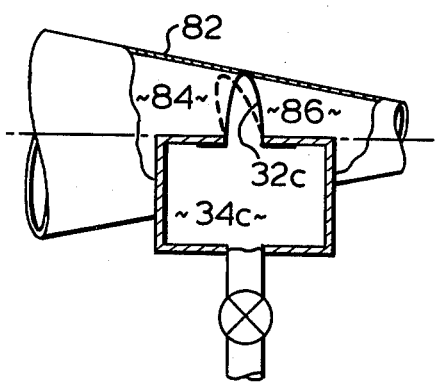
FIG. 12 illustrates a further pneumatic pressure release valve suitable for use in a negative pressure system such as that described with reference to FIG. 11.

FIG. 12 of the drawings shows an alternative construction in which passage 82 tapers from an enlarged diameter 84 on the low pressure side to a reduced diameter in the passage 86 on the high pressure side. Again this facilitates the movement of the diaphragm 32c between its open and closed positions. It will be apparent that as the pressure in the passage 84 decreases in relation to the pressure in the chamber 34c, the diaphragm 32c may tend to expand if it is made from an elastic material. Such expansion would tend to wedge the diaphragm in a closed position in a passage of uniform cross-sectional area.

It will be apparent that the pressure release device of FIGS. 11 and 12 of the drawings may be used in the positive pressure applications referred to above with reference to FIGS. 2 through 10 of the drawings. In such applications, the passage 84 will be connected to the system in which the pressure is to be controlled with the passage 86 being vented to atmosphere or to a reservoir of the occluded medium used in the system.

The tubular portion 30 and the walls of the pressure chamber 34 are preferably made from a transparent plastic material so that the operation of the valve can be visually observed by the operator.

In describing the preferred embodiments, the valve has been described as used in a number of medical applications. It will, however, be apparent that the pressure release valve of the present invention may be used in any number of industrial or commercial applications for controlling the pressure in any fluid conveying line. It will also be apparent that the fluid may not necessarily be air.

Figure 13:
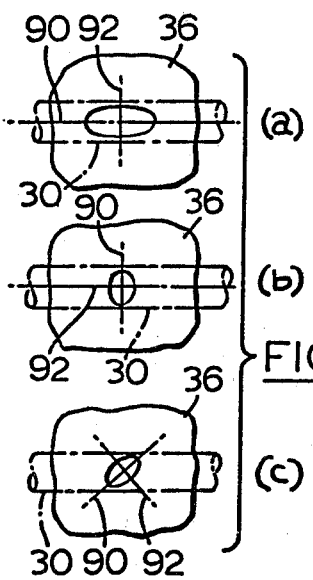
FIGS. 13a, 13b and 13c illustrate alternative configurations of the valve passage opening into the through passage of the valve.

In the preferred embodiment described above, the valve passage which communicates between the pressure chamber 34 and the through passage 44 is illustrated as being of a circular configuration. Alternative configurations may, however, be employed to advantage in certain applications. For example, when the fluid in the through passage 44 is at a high pressure the valve passage may conveniently be of an oval shape as shown in FIG. 13a with the major axis 90 extending in the longitudinal direction of the through passage 44 and the minor axis 92 extending transversely of the through passage 44. In low pressure systems, the valve passage 44 may be of an oval configuration as shown in FIG. 13b with the major axis 90 extending transversely and the minor axis 92 extending longitudinally with respect to the through passage 44. In yet another variation, FIG. 13c, the valve passage may have its major axis 90 extending obliquely across the through passage 44. It should be noted that the valve passage, in negative pressure applications, should not have a major axis extending in the longitudinal direction of the through passage as the valve closure member would not necessarily collapse inwardly to open the through passage in such a construction. Preferably, in negative pressure applications the cross-sectional area of the through passage is greater on the negative side of the diaphragm so that opening may be achieved by angular deflection of the diaphragm rather than inward collapsing of the diaphragm.

From the foregoing, it will be apparent that the pneumatic valve of the present invention is of a simple construction and is simple to operate and maintain. The operation of the valve is unaffected by its position or by the position of the system to which it is connected in use. The valve may be used to maintain the pressure in the system at any predetermined level. The valve is capable of releasing pressures in excess of the preset pressure if the pressure in the system increases above the preset pressure. The valve can be regulated with ease and its function can be visually checked when it is constructed of a suitable transparent material. The generation of a positive end expiratory pressure in any clinical setting, such as in an operating room, can be achieved with ease in an intubated patient. The valve may be used to regulate both positive and negative pressures. Two or more pneumatic valves according to the present invention may be used in any system to permit the system to operate within a wide pressure range as described in FIG. 9 of the drawings. Also as indicated in the drawings various systems can be developed for providing simultaneous pressurization of the system and the pressure chamber.

Figure 14:
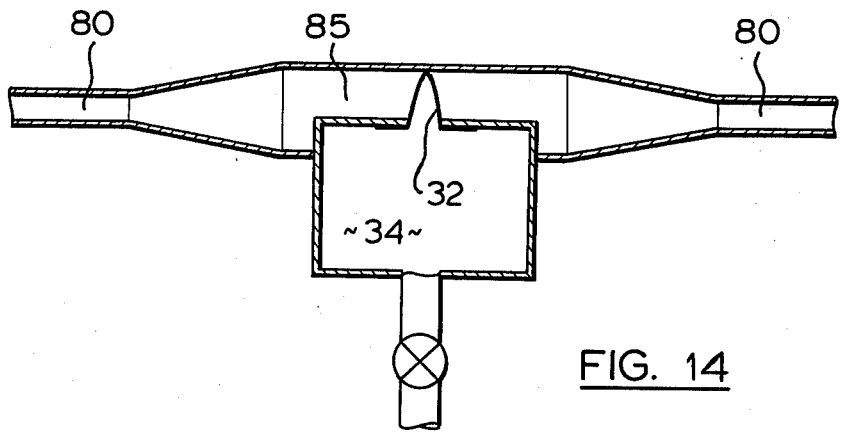
FIG. 14 is a diagrammatic illustration of a pneumatic pressure release valve according to a further embodiment.

In the embodiment of the invention illustrated in FIG. 2 of the drawings, the valve closure member 32 is designed to operate in a semi-circular portion of the through passage. Thus the cross-sectional area of the through passage is substantially reduced in the area of the valve member. Such a reduction may be undesirable in certain applications. It may be particularly undesirable in a pressure system in which the medium in the through passage is a liquid. To overcome this difficulty, the through passage may be constructed as shown in FIG. 14 of the drawings in which it includes a central portion 85 of a cross-sectional area which is substantially greater than that of the remainder of the through passage 80 on either side thereof. By enlarging the through passage at the valve in this manner, the valve is capable of opening to an extent sufficient to provide an opening in the through passage of a cross-sectional area which is at least as great as that of the remainder of the through passage.

These and other applications of the pneumatic valve of the present invention will be apparent to those skilled in the art.

For example, two or more of the pneumatic valves of the present invention may be connected in series or in parallel in order to increase the reliability of any of the systems described above.

What I claim as my invention is:

1. An inflatable cuff system for a tracheal or endotracheal tube or the like, comprising:
   (a) an inflatable cuff,
   (b) an inflation passage communicating with said cuff by means of which the cuff may be inflated by an inflating medium,
   (c) a pressure releasing first valve and a pressure releasing second valve arranged in series with one another in the inflation passage for regulating the flow of inflating medium through the inflation passage,
   (d) said first and second valves being spaced from one another to provide a reservoir for inflating medium therebetween,
   (e) said first valve being located between said cuff and said reservoir and being set to open to permit inflating medium to escape from said cuff into said reservoir when the pressure in the cuff rises above a predetermined first pressure,
   (f) said second valve being located outwardly from said reservoir in relation to the cuff and being set to open to permit inflating medium to escape from said reservoir when the pressure in the reservoir rises above a predetermined second pressure which is greater than said first pressure whereby at least a portion of the inflating medium displaced from the cuff into the reservoir may be retained in the reservoir at a pressure up to said second pressure and may be returned to said cuff when the pressure in the cuff drops below the pressure in the reservoir.

2. An inflatable cuff system as claimed in claim 1 wherein said reservoir includes a reservoir chamber, an input passage opening into said reservoir chamber and valve means for selectively opening and closing said input passage.

3. An inflatable cuff system as claimed in claim 2 wherein the walls of said reservoir are flexible to expand the capacity of said reservoir as the pressure in said reservoir rises above a predetermined pressure.

4. An inflatable cuff system as claimed in claim 1 wherein said first valve and said second valve are each pneumatic valves comprising a pressure chamber, a valve closure member adapted to open and close said inflation passage in response to a pressure differential between said inflation passage and said pressure chamber, input passage means opening into said pressure chamber for admitting a pressurizing medium to said pressure chamber to pressurize said chamber to set the pressure at which the valve closure member will open to vent said inflatable cuff system, and means for selectively opening and closing said input passage means.

* * * * *